United States Patent [19]
Okawa et al.

[11] Patent Number: 6,140,525
[45] Date of Patent: Oct. 31, 2000

[54] HYPERBRANCHED POLYMERS AND METHODS FOR THE PREPARATION THEREOF

[75] Inventors: Tadashi Okawa, Chiba Prefecture, Japan; Aziz Muzafarov, Moscow, Russian Federation; Stephen Cray, Sully, United Kingdom

[73] Assignees: Russian Academy of Sciences, Moscow, Russian Federation; Dow Corning Corporation, Midland, Mich.; Dow Corning Toray Silicone Co., Tokyo, Japan

[21] Appl. No.: 09/218,274

[22] Filed: Dec. 21, 1998

Related U.S. Application Data

[63] Continuation-in-part of application No. 08/977,291, Nov. 24, 1997, abandoned.

[51] Int. Cl.$^7$ ....................................................... C07F 7/08
[52] U.S. Cl. ........................ 556/434; 556/451; 556/452; 528/15; 528/28; 528/31
[58] Field of Search .................................... 556/451, 452, 556/434; 528/25, 28, 31

[56] References Cited

U.S. PATENT DOCUMENTS 6,001,945  12/1999  Decker et al. ...................... 556/436 X

FOREIGN PATENT DOCUMENTS 3-263431  3/1990  Japan .

OTHER PUBLICATIONS

Journal of Inorganic and Organometallic Polymers, 4(1), pp. 61–77, (1994).

*Primary Examiner*—Paul F. Shaver
*Attorney, Agent, or Firm*—Timothy J. Troy; Robert L. McKellar

[57] ABSTRACT

This invention relates to a macromonomer and a method for its preparation. The macromonomer has silicon-bonded hydrogen atoms at one molecular chain terminal, and aliphatically unsaturated silicon-bonded organic groups at the other molecular chain terminal. This invention further related to a method of forming a hyperbranched polymer by polymerizing the macromonomer with a group VIII metal catalyst. The hyperbranched polymers can be used as surfactants, gelling agents, drug delivery systems, and polymeric absorbents.

37 Claims, No Drawings

HYPERBRANCHED POLYMERS AND METHODS FOR THE PREPARATION THEREOF

This application is a continuation-in-part of U.S. patent application Ser. No. 08/977,291 filed on Nov. 24, 1997 abandoned.

FIELD OF THE INVENTION

This invention relates to hyperbranched polymers and methods for their preparation by polymerization of macromonomers. This invention further relates to a macromonomer and to a method for its preparation.

BACKGROUND OF THE INVENTION

Hyperbranched refers to a class of very highly branched polymers which tend to be globular in form. Various types of hyperbranched polymers, which are represented by the Starburst™ dendrimers (treelike polymers), are known. These hyperbranched polymers have higher functional group densities per molecular unit than straight-chain polymers and conventional branched polymers. Another characteristic feature of the hyperbranched polymers is that they possess an internal space once they have been elaborated to several generations. These characteristics point to potential applications as surfactants, gelling agents, drug delivery systems, polymeric absorbents, and the like.

Additionally, introduction of the siloxane bond into the hyperbranched polymer format could provide a hyperbranched polymer that possesses the unique features of polysiloxanes. Various polysiloxane-based hyperbranched polymers have already been proposed. Hyperbranched siloxane polymers can have a SiH surface or an alkenyl or alkynyl surface. However, it is difficult to prepare hyperbranched polymers with a SiH surface because of several factors, including the instability of the SiH precursors, difficulty in controlling the reaction to prevent crosslinking, and difficulty in preventing side reactions during storage. For example, JP-A 03-263,431 teaches a method for synthesizing a SiH-functional polysiloxane dendrimer by repeating a multi-step reaction that includes condensation of the SiCl and SiOH groups and hydrolysis of the SiH group. This method, however, is unsuitable for large-scale industrial production due to its complex synthetic procedure and low overall yield.

In *Organometallic News*, 40–42 (1993), a method is proposed for the synthesis of a SiH-functional polysiloxane dendrimer by reacting polyfunctional chlorosilane with 1,1,3,3-tetramethyldisiloxane in the presence of hydrochloric acid to replace the chlorine atom of SiCl with the dimethylsiloxy group. Since these synthetic methods are each multi-step reactions with isolation and purification at each step, they offer the advantage of producing dendrimers with defined structures and narrow molecular weight distributions. However, they require repetition of the reaction process a number of times in order to obtain dendrimer of the desired generation and they have low overall yields, and these features make them very unsuitable for large-scale industrial production.

Hyperbranched poly(siloxysilanes) are described by Mathias and Carothers in J. Am. Chem. Soc. 1991, 113, 4043–4044. A monomer of the formula $Vi(CH_2)Si(OSiMe_2H)_3$, where Vi is vinyl and Me is methyl, is polymerized using a platinum hydrosilation catalyst. The resulting hyperbranched polymer with a SiH surface can be stabilized by capping with allylphenylether.

In contrast, in *J. Inorg. Organomet. Polym.* 4(1), 61–77 (1994) a single-step method is proposed for obtaining SiH-functional or Si-vinyl-functional hyperbranched polysiloxane by the intermolecular hydrosilylation reaction of vinyltris(dimethylsiloxy)silane or tris(vinyldimethylsiloxy) silane. While this method cannot provide a narrow molecular weight distribution or defined-structure dendrimer, it nevertheless offers the advantage of providing a Si-functionalized hyperbranched polysiloxane in a single step and has the potential for large-scale industrial production.

Due to the close proximity of the silicon-bonded hydrogen and vinyl in this method, steric hindrance increases in association with the development of the hydrosilylation reaction to such a degree that bringing the reaction to completion becomes quite problematic. In addition, this method has been unable to bring the properties characteristic of polysiloxanes to the hyperbranched polymer format because it gives polymer that has the silethylenesiloxane structure.

As a consequence, a highly reactive, SiH-functional polysiloxane that can provide SiH-functional hyperbranched polysiloxane in a single step is desired. Specifically, an object of the present invention is to provide an organopolysiloxane macromonomer and a method for its preparation. The macromonomer carries an aliphatically unsaturated organic group at one molecular chain terminal and silicon bonded hydrogen atoms at the other terminal. A further object of the invention is to provide a hyperbranched polymer by polymerizing the macromonomer. A further object of this invention is to provide a method for stabilizing the monomer.

SUMMARY OF THE INVENTION

This invention relates to a macromonomer and a method for its preparation. The macromonomer has silicon-bonded hydrogen atoms at one molecular chain terminal, and aliphatically unsaturated silicon-bonded organic groups at the other molecular chain terminal. This invention further relates to a method of forming a hyperbranched polymer by contacting the macromonomer with a group VIII metal catalyst. This invention further relates to a method for stabilizing the hyperbranched polymer.

DETAILED DESCRIPTION OF THE INVENTION

This invention relates to a macromonomer and method for its preparation. The macromonomer has the general formula:

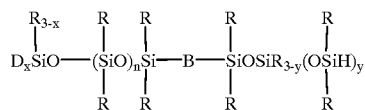

wherein D is an aliphatically unsaturated organic group, each R is independently selected from the group consisting of monovalent hydrocarbon groups with no aliphatic unsaturation and monovalent halogenated hydrocarbon groups with no aliphatic unsaturation; B is selected from the group consisting of an oxygen atom and a divalent hydrocarbon group of at least two carbon atoms and with no aliphatic unsaturation; n is an integer with a value greater than or equal to 0; x is 1, 2, or 3; y is 1, 2, or 3; with the provisos that when x is 1, y is 2 or 3 and when y is 1, x is 2 or 3.

D represents an aliphatically unsaturated organic group, for example, alkenyl such as vinyl, butenyl, and hexenyl;

alkenyloxyalkyl such as allyloxyethyl, methacryloxypropyl, and 4-vinylphenyl. D is preferably a lower alkenyl or alkynyl group containing 2 to 6 carbon atoms. D is more preferably vinyl or allyl, with the proviso that the unsaturation of the allyl group is terminal. Vinyl is particularly preferred due to ease of synthesis and economics.

Each R is independently selected from the group consisting of monovalent hydrocarbon groups with no aliphatic unsaturation and monovalent halogenated hydrocarbon groups with no aliphatic unsaturation. Examples of monovalent hydrocarbon groups for R include alkyl such as methyl, ethyl, propyl, butyl, pentyl, and hexyl; aryl such as phenyl, tolyl, and xylyl; and aralkyl such as benzyl and phenethyl. Monovalent halogenated hydrocarbon groups are exemplified by trifluoropropyl. R is preferably independently selected from the group consisting of alkyl groups of 1 to 6 carbon atoms, haloalkyl groups of 1 to 6 carbon atoms, and phenyl. Methyl is particularly preferred for R.

B is selected from the group consisting of oxygen and divalent hydrocarbon groups with at least 2 carbon atoms and no aliphatic unsaturation. B is exemplified by ethylene, methylmethylene, propylene, butylene, and hexylene. B is preferably ethylene.

The subscript x has a value of 1, 2, or 3, the subscript y has a value of 1, 2, or 3; with the provisos that when x is 1, y is 2 or 3, and when y is 1, x is 2 or 3. When x is 1, y is 2 or 3, and the macromonomer will have one aliphatically unsaturated organic group at one molecular chain terminal and 2 or 3, respectively, diorganohydrogensiloxy groups at the other molecular chain terminal. When y is 1, x is 2 or 3, and the macromonomer will have one diorganohydrogensiloxy group at one molecular chain terminal and 2 or 3, respectively, aliphatically unsaturated organic groups at the other molecular chain terminal.

The subscript n is an integer greater than or equal to 0. Preferably, n ranges from 0 to 1,000, more preferably from 0 to 200, more preferably 1 to 100, and particularly preferably from 10 to 100.

A preferred macromonomer of this invention has the formula

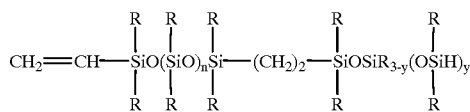

where R, n, and y are as described above.

A particularly preferred macromonomer of this invention has the formula

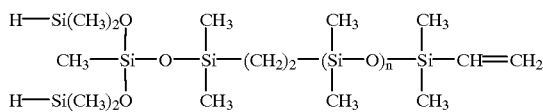

where n is preferably 10 to 100.

This invention further relates to a method for making the macromonomer. The method comprises (I) reacting component (a), which has general formula

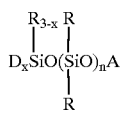

where D, R, and n are as defined above, and A is selected from the group consisting of a hydrogen atom, an alkali metal atom, and combinations thereof; and component (b), which has general formula

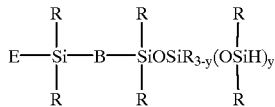

where R, B, and y are as defined above and E is selected from the group consisting of halogen atoms, amino groups, substituted amino groups, and acyloxy groups. Preferably, the halogen atom is chlorine and the alkali metal atom is lithium.

Component (a) may be an organosilane or an organosiloxane or a mixture thereof. Component (a) can be synthesized by the living polymerization of cyclic hexaorganotrisiloxane using a lithium metal salt of an aliphatically unsaturated silanol or siloxanol or a partially lithiated aliphatically unsaturated silanol or siloxanol. Synthesis of component (a) by this method is described in U.S. Pat. No. 4,976,373, hereby incorporated by reference. When A is a hydrogen atom, component (a) is an organopolysiloxane bearing silanol at one molecular chain terminal. This type of component (a) can be synthesized by treating the α-lithiooxyorganopolysiloxane or partially lithiated α-hydroxyorganopolysiloxane synthesized as described above with, for example, acetic acid or carbonic acid.

Component (b) is an organosilicon compound. The hydrolyzable group, E, on component (b) is selected from the group consisting of halogen atoms, alkali metal atoms, amino groups, substituted amino groups, and acyloxy groups. The hydrolyzable group is specifically exemplified by halogen atoms such as fluorine, chlorine, bromine, and iodine; the amino group; substituted amino groups such as ethylamino, diethylamino, substituted silylamino, and substituted siloxanylamino; and acyloxy groups such as acetoxy and propionyloxy.

Silazane derivatives with the structures given below can be used as component (b) in this invention. The silazanes can be synthesized by reacting ammonia and the corresponding chlorosiloxane compound, as shown in the following equation:

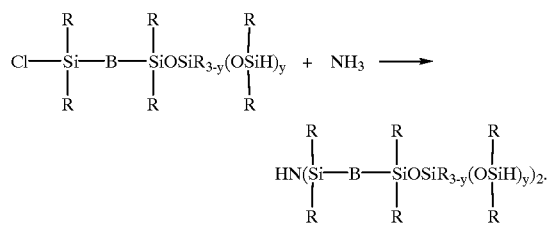

Alternatively, the silazanes can be synthesized by a hydrosilylation reaction between silazane containing aliphatically unsaturated bonding and oligosiloxane bearing multiple SiH functionalities, as shown in the following equation:

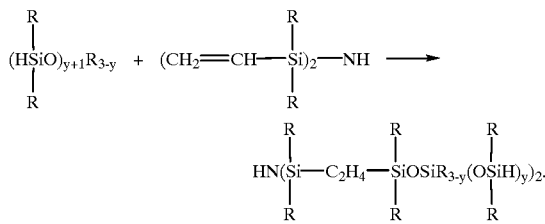

Among the examples of E, the chlorine atom and diethylamino group are preferred due to ease of synthesis, reactivity, and economics. The chlorine atom is particularly preferred.

Alternatively, component (b) can be synthesized by addition reaction of a silicon compound that contains 3 or 4 diorganohydrogensiloxy groups in each molecule with a silane that contains an Si-bonded hydrolyzable group and aliphatically unsaturated bonding in the same molecule and by subsequent purification by distillation to isolate the 1:1 adduct. The 1:1 adduct can be obtained in good yields from this reaction by improving the reaction selectivity with at least the stoichiometric amount of the former reagent relative to the latter reagent. A stoichiometric ratio in the range of equivalency to 3-times equivalency is preferred.

This addition reaction is catalyzed by a catalyst comprising a Group VIII metal that is suitable for use in hydrosilylation reactions. Examples of suitable catalysts are ruthenium, rhodium, palladium, osmium, iridium and platinum. Preferably the catalyst is a platinum compound or complex. Suitable platinum compounds and complexes include chloroplatinic acid and its alcohol solutions, platinum acetylacetonate, complexes of platinous halides with unsaturated compounds such as ethylene, propylene, organovinylsiloxanes, and styrene, hexamethyldiplatinum, $PtCl_2$, $PtCl_3$, $PtCl_4$, and $Pt(CN)_3$.

The addition reaction can be run in the absence of solvent or in a suitable organic solvent. Specific examples of organic solvents include aromatic hydrocarbons such as benzene, toluene, and xylene; aliphatic hydrocarbons such as hexane and heptane; ethers such as tetrahydrofuran and diethyl ether; ketones such as acetone and methyl ethyl; esters such as ethyl acetate and butyl acetate; chlorinated hydrocarbons such as carbon tetrachloride, trichloroethane, and chloroform; as well as dimethylformamide and dimethyl sulfoxide. This addition reaction can be run at room temperature, but it is preferably run at 50° C. to 200° C.

Alternatively, components (a) and (b) can be reacted by condensation reaction. The condensation reaction between components (a) and (b) should be run using at least one equivalent of component (b) relative to component (a) and preferably at least 1.05 equivalents of component (b) relative to component (a). The condensation reaction is preferably run at 0° C. to 200° C. and more preferably at 20° C. to 100° C. The condensation reaction can be run without solvent, but it is preferably run in the presence of a suitable organic solvent. Suitable organic solvents are specifically exemplified by aromatic hydrocarbons such as benzene, toluene, and xylene; aliphatic hydrocarbons such as hexane and heptane; ethers such as tetrahydrofuran and diethyl ether; ketones such as acetone and methyl ethyl ketone; esters such as ethyl acetate and butyl acetate; chlorinated hydrocarbons such as carbon tetrachloride, trichloroethane, and chloroform; as well as dimethylformamide and dimethyl sulfoxide.

When component (a) is a mixture that contains both hydrogen and alkali metal atoms for different instances of A, and component (b) is an organosilicon compound in which E is a halogen atom, an amine compound is preferably added as a hydrogen halide scavenger to inhibit equilibration reactions by the organopolysiloxane chain under the influence of the hydrogen halide by-product generated by this reagent combination. These amine compounds are exemplified by triethylamine, diethylamine, and pyridine.

When component (b) is an organosilicon compound in which E is an amino group or a substituted amino group, A in component (a) is limited to the hydrogen atom. This reaction will run in the absence of catalyst, but a small amount of an acidic compound such as trifluoroacetic acid, trimethylchlorosilane, or ammonium chloride, can also be added as catalyst to accelerate the reaction rate.

When component (a) is a mixture that contains both hydrogen and alkali metal atoms for different instances of A, and component (b) is an organosilicon compound in which E is an acyloxy group, an amine compound is preferably added as a carboxylic acid scavenger to inhibit equilibration reactions by the organopolysiloxane chain under the influence of the carboxylic acid by-product generated by this reagent combination. These amine compounds are exemplified by triethylamine, diethylamine, and pyridine.

This invention further relates to an alternative method for preparing the macromonomer. This method comprises reacting component (a') which has the general formula

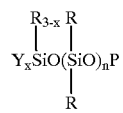

where D, R, and n are as defined above, and P is selected from the group consisting of halogen atoms and alkali metal atoms; and component (b'), which has the general formula

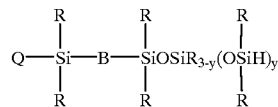

where R, B, and y are as defined above and Q is selected from the group consisting of alkali metal atoms and halogen atoms; with the provisos that when P is an alkali metal atom, Q is a halogen atom; and when Q is an alkali metal atom, P is a halogen atom. The halogen atom is preferably chlorine, and the alkali metal atom is preferably lithium.

Preferably, component (a') has formula $Li(OSiR_2)_n$—$CH{=}CH_2$ and component (a') is formed by reacting $CH_2{=}CHSiR_2OLi$ with $(R_2SiO)_3$ in proportions predetermined to obtain the desired value of n described above.

In a preferred embodiment, and component (a') has the formula $Li(OSiR_2)_n$—$CH{=}CH_2$, and component (b') is a compound of the formula:

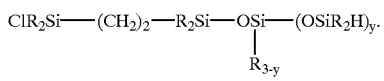

In a particularly preferred embodiment, y=2 and component (b') has formula

wherein component (b') is formed by reacting

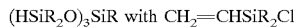

in the presence of a platinum catalyst.

The catalyst comprising a group VIII metal which may be employed in the preparation of the macromonomer, and also in the polymerization of the macromonomer, is any such catalyst suitable for use in hydrosilylation reactions. Examples of suitable catalysts are ruthenium, rhodium, palladium, osmium, iridium and platinum. Preferably the catalyst is a platinum compound or complex. Suitable platinum compounds and complexes include chloroplatinic acid, platinum acetylacetonate, complexes of platinous halides with unsaturated compounds such as ethylene, propylene, organovinylsiloxanes, and styrene, hexamethyldiplatinum, $PtCl_2$, $PtCl_3$, $PtCl_4$, and $Pt(CN)_3$.

This invention further relates to a method for preparing a hyperbranched polymer by polymerizing the macromonomer with a group VIII metal catalyst, e.g. platinum, catalysts. Suitable group VIII metal catalysts are disclosed above.

For macromonomers having a single aliphatically unsaturated group D and two or three SiH groups, 100% conversion of the aliphatically unsaturated groups can be achieved after several hours. The molecular masses of the reaction products depend on several factors, particularly the type of macromonomer and the concentration of macromonomer and catalyst in solution.

Macromonomers having a single aliphatically unsaturated group D and two or three SiH groups, will polymerize to form a hyperbranched polymer with an SiH surface. When the hyperbranched polymer has an SiH surface, it can be stabilized by addition of a volatile SiH-containing compound or by extracting platinum-containing compounds using an immiscible nitrogen-containing polar solvent. The volatile SiH-containing compound may be trimethylsilane or tetramethyldisiloxane. The solvent may be tetramethylethylenediamine, polyethylenepolyamine or acetonitrile.

This invention further relates to a method for stabilizing the hyperbranched polymers. To stabilize the hyperbranched polymers, control is preferably effected over catalyst concentration minimization and reaction mixture dilution. On completion of reaction, the Group VIII metal, e.g. platinum, catalyst is preferably deactivated or a low molecular weight SiH compound is added.

EXAMPLES

These examples are intended to illustrate the invention to those skilled in the art and should not be interpreted as limiting the scope of the invention set forth in the claims.

For macromonomers having a single aliphatically unsaturated group D and two or three SiH groups, 100% conversion of the aliphatically unsaturated groups can be achieved after several hours. The molecular masses of the reaction products depend on several factors, particularly the type of macromonomer and the concentration of macromonomer and catalyst in solution. In the case of a relatively small macromonomer, such as MM-1 in the examples below, experiments with a 50% solution of the macromonomer in n-hexane show full conversion of vinyl groups and 50% conversion of SiH groups, and the molecular mass of the product coincides with the molecular mass of the macromonomer. This can be explained by a cyclization process only. In bulk, a soluble polymer with a molecular mass range of 15,000 to 30,000 was obtained.

With larger macromonomers (such as MM-2 and MM-3 in the examples below) reactions in bulk may lead to obtaining crosslinked insoluble products. In the case of polymerization in solution, both these macromonomers after full conversion of vinyl groups gave soluble polymers. The most probable side reaction, leading to crosslinking, is interaction of functional groups with platinum catalyst with subsequent regrouping. Decreasing the catalyst concentration allows for obtaining fully soluble products at total conversion of vinyl groups.

Hyperbranched H-functional hyperbranched polydimethylsiloxanes and similar products based on the macromonomers of this invention. The obtained hyperbranched polymers are transparent slow-moving liquids. The intrinsic viscosity of the obtained hyperbranched polymers varies from 0.15 to 0.65 dl/g and molecular masses of from 15,000 to 800,000, depending on the size of the initial macromonomer.

Example 1

Hydrogen functional trisiloxymethylsilane was reacted with vinylchlorodimethylsilane in toluene in the presence of a platinum catalyst in accordance with the following equation to produce the intermediate (I):

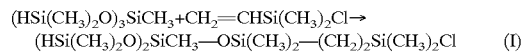

Lithiumvinylsilanoate was reacted with cyclic trisiloxane in a solvent mixture of 96% toluene and 4% dimethylformamide to form the intermediate (II) in accordance with the following equation:

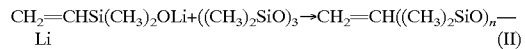

The value of n in the intermediate (II) is controlled by the ratio of amounts of reagents in this step. The intermediates (I) (103 mmol) and (II) (85 mmol) are then reacted together in 220 g of a mixture of 96% toluene and 4% dimethylformamide with elimination of lithiumchloride over a period of 15 hours in accordance with the following equation:

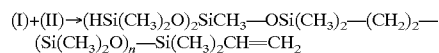

Three macromonomers were prepared with properties as set out in Table 1 below:

TABLE 1

Macromonomers parameters

| Macromonomer | n | $M_{calk}$ | $M_{GPC}$ | $M_w/M_n$ | $M_{PMR}$ |
|---|---|---|---|---|---|
| MM-1 | 10 | 1046 | 1120 | 1.16 | 1192 |
| MM-2 | 50 | 4006 | 4310 | 1.07 | 5480 |
| MM-3 | 100 | 7706 | 7720 | 1.03 | 7940 |

The macromonomers were analyzed by IR and NMR spectroscopy and by GPC.

The samples had a narrow molecular mass distribution and a good relation between calculated and experimental data for molecular mass.

Example 2

Polyaddition of Macromonomer in Bulk

To 20 g ($2.10^{-2}$ mol) of macromonomer MM-1 in a flask under argon was added 10 ml of solution of Pt-catalyst PC072 ($1.5.10^{-3}\%$ mass Pt) via a syringe. The reaction was followed by taking of probes for $^1H$ NMR. In 24 hours at room temperature the reaction ended. GPC: monomodal molar mass distribution. After precipitation of 5% hexane solution by ethanol 80% mass of polymer was obtained with MM about 15000.

Example 3

Polyaddition of Macromonomer in Solution

To 30% hexane solution of macromonomer MM-2 20 g ($5.10^{-3}$ mol) under argon was added 10 ml of solution of Pt-catalyst PC072 ($2.10^{-3}\%$ mass Pt) via a syringe. In 24 hours at room temperature the reaction was over by the data of $^1H$ NMR-spectra. GPC: monomodal molar mass distribution with maximum of curve about 35000.

Following the procedures of Examples 2 and 3 above, further polyaddition processes were carried out with the results shown in Table 2 below:

TABLE 2

Results of polyaddition processes (TMEDA is tetramethylethylenediamine.PEPA is polyethylenepolyamine.)

| Ex | Macromonomer | concentration mass % | Cat., mass % | Time of reaction h | Conversion of vinyl groups, % | Mole mass by GPC data | Intrinsic viscosity [O], dl/g | life time, h |
|---|---|---|---|---|---|---|---|---|
| 4 | MM-1 | 25 | Pt $2*10^{-3}$ | 48 | 100 | 1000 | 0,085 | " |
| 5 | " | " | " | 72 | 100 | 1000 | — | " |
| 6 | " | bulk | " | 72 | 100 | 15000 | — | " |
| 7 | " | bulk | $1,5 * 10^{-3}$ | 24 | 100 | 15000 | — | " |
| 8 | " | 33 | $1,5 * 10^{-3}$ | 240 | 100 | 1000 | — | " |
| 9 | MM-2 | 25 | Pt $2 * 10^{-3}$ | 48 | 100 | 35000 | 0,48 | ~200 |
| 10 | " | 30 | $2 * 10^{-4}$ | 96 | 0 | — | — | — |
| 11 | " | bulk | $2 * 10^{-4}$ | 72 | 100 | gel | — | — |
| 12 | " | bulk | $2 * 10^{-4}$ | 24, with adding HSiMe$_3$ | 100 | 10000 | — | no gel |
| 13 | " | 34 | $1,5 * 10^{-3}$ | 48 | 100 | 3500 | — | ~200 |
| 14 | " | " | " | 48, with adding HSiMe$_3$ | " | " | – | no gel |
| 15 | " | 30 | $2 * 10^{-4}$ | 72 | 100 | 12000 | 0,19 | ~300 |
| 16 | " | bulk | $1,5 * 10^{-3}$ | 24 | 100 | gel | — | — |
| 17 | MM-3 | bulk | Pt $2 * 10^{-3}$ | 24 | 100 | gel | — | — |
| 18 | " | bulk | $2 * 10^{-4}$ | 24 | 100 | gel | — | — |
| 19 | " | 30 | $2 * 10^{-3}$ | 48 | 100 | 80000 | 0,64 | ~100 |
| 20 | " | 5 | $3 * 10^{-3}$ | 48 | 100 | " | — | ~1000 in solution |
| 21 | " | 10 | " | 48 | 100 | " | — | ~200 |
| 22 | " | 25 | " | 48 | 100 | " | — | ~100 |
| 23 | " | 3 | $1,5 * 10^{-3}$ | 48 | 100 | 80000 | — | no gel in solution |
| 24 | " | 3 | $0,6 * 10^{-3}$ | 48 | 100 | 80000 | — | no gel in solution |
| 25 | " | 28 | $1,5 * 10^{-3}$ | 48 | 100 | " | — | ~100 |
| 26 | " | 28 | $1,5 * 10^{-3}$ | 48, with adding HSiMe$_3$ | 100 | " | — | no gel |
| 27 | " | 28 | $1,5 * 10^{-3}$ | 48, with washing by TMEDA | 100 | " | — | no gel |
| 28 | " | 28 | $1,5 * 10^{-3}$ | 48, with washing by PEPA | 100 | " | — | no gel |
| 29 | " | 30 | $3 * 10^{-4}$ | 48 | 100 | 70000 | 0,64 | 100 |

We claim:

1. A macromonomer having a general formula

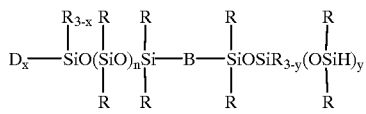

wherein D is an aliphatically unsaturated organic group, each R is independently selected from the group consisting of monovalent hydrocarbon groups with no aliphatic unsaturation and monovalent halogenated hydrocarbon groups with no aliphatic unsaturation; B is selected from the group consisting of an oxygen atom and a divalent hydrocarbon group of at least two carbon atoms and with no aliphatic unsaturation; n is an integer with a value greater than or equal to 0; x is 1, 2, or 3; y is 1, 2, or 3; with the provisos that when x is 1, y is 2 or 3 and when y is 1, x is 2 or 3.

2. The macromonomer of claim 1, wherein each R is independently selected from the group consisting of alkyl, haloalkyl, and aryl groups.

3. The macromonomer of claim 2, wherein each R is independently selected from the group consisting of alkyl groups of 1 to 6 carbon atoms, haloalkyl groups of 1 to 6 carbon atoms, and phenyl groups.

4. The macromonomer of claim 3, wherein R is methyl.

5. The macromonomer of claim 1, wherein D is selected from the group consisting of alkenyl-containing groups and alkynyl-containing groups.

6. The macromonomer of claim 5, wherein D is selected from the group consisting of lower alkenyl groups and alkynyl groups of 2 to 6 carbon atoms.

7. The macromonomer of claim 6, wherein D is selected from the group consisting of vinyl and allyl, with the proviso that the unsaturation of the allyl group is terminal.

8. The macromonomer of claim 1, wherein n is 10 to 100.

9. The macromonomer of claim 1, wherein B is a divalent hydrocarbon group of at least 2 carbon atoms with no aliphatic unsaturation.

10. The macromonomer of claim 9, wherein B is selected from the group consisting of ethylene, methylmethylene, propylene, butylene, and hexylene.

11. The macromonomer of claim 1, wherein the macromonomer has formula:

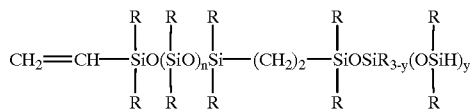

wherein R and n are as described above, and y is 2 or 3.

12. The macromonomer of claim 11, wherein the macromonomer has formula:

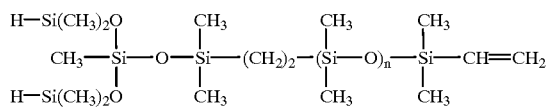

wherein n has a value of 10 to 100.

13. A method comprising: (I) reacting components (a) and (b) to form a product; wherein component (a) has formula

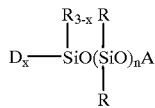

wherein D is an aliphatically unsaturated organic group, each R is independently selected from the group consisting of monovalent hydrocarbon groups with no aliphatic unsaturation and monovalent halogenated hydrocarbon groups with no aliphatic unsaturation; n is an integer with a value greater than or equal to 0; x is 1, 2, or 3; and A is selected from the group consisting of a hydrogen atom, an alkali metal atom, and combinations thereof; and component (b) has formula

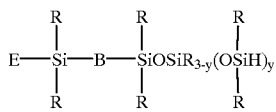

where R is as defined above; B is selected from the group consisting of an oxygen atom and a divalent hydrocarbon group with at least 2 carbon atoms and no aliphatic unsaturation; E is selected from the group consisting of halogen atoms, amino groups, substituted amino groups, and acyloxy groups; y is 1, 2, or 3; with the provisos that when x is 1, y is 2 or 3 and when y is 1, x is 2 or 3; and when E is an amino group or a substituted amino group, A is hydrogen.

14. The method of claim 13, wherein when component (a) is a mixture comprising both hydrogen and alkali metal atoms for different instances of A and E is a halogen atom, the method further comprises adding an amine compound to the product of (I).

15. The method of claim 14, wherein the amine compound is selected from the group consisting of triethylamine, diethylamine, and pyridine.

16. The method of claim 13, wherein when E is an amino group or a substituted amino group and A is hydrogen, the method further comprises adding a small amount of an acidic compound to components (a) and (b).

17. The method of claim 16, wherein the acidic compound is selected from the group consisting of trifluoroacetic acid, trimethylchlorosilane, and ammonium chloride.

18. The method of claim 13, wherein when component (a) is a mixture comprising both hydrogen and alkali metal atoms for different instance of A and E is an acyloxy group, the method further comprises adding an amine compound to the product of (I).

19. The method of claim 18, wherein the amine compound is selected from the group consisting of triethylamine, diethylamine, and pyridine.

20. The method of claim 13, wherein E is selected from the group consisting of a chlorine atom and a diethylamino group.

21. The method of claim 20, wherein E is a chlorine atom.

22. The method of claim 13, wherein component (b) has the formula

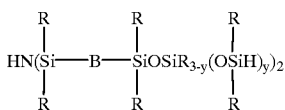

wherein R, B, and y are as described above.

23. The method of claim 13, wherein at least 1 equivalent of component (b) based on component (a) is present.

24. The method of claim 23, wherein there is at least 1.05 equivalent of component (b) based on component (a).

25. The method of claim 13, wherein reacting components (a) and (b) is carried out in the presence of organic solvent.

26. The method of claim 13, wherein reacting components (a) and (b) is carried out at 0 and 200° C.

27. The method of claim 26, where reacting components (a) and (b) is carried out at 20 to 100° C.

28. A method of preparing a macromonomer, wherein the method comprises (I) reacting components (a') and (b'); wherein component (a') has general formula

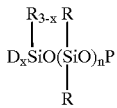

wherein D is an aliphatically unsaturated organic group, each R is independently selected from the group consisting of monovalent hydrocarbon groups with no aliphatic unsaturation and monovalent halogenated hydrocarbon groups with no aliphatic unsaturation; n is an integer with a value greater than or equal to 0; x is 1, 2, or 3; and P is selected from the group consisting of halogen atoms and alkali metal atoms; and component (b') has general formula

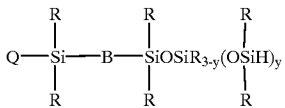

where R, is as defined above; B is selected from the group consisting of an oxygen atom and a divalent hydrocarbon group with at least 2 carbon atoms and no aliphatic unsaturation; y is 1, 2, or 3, Q is selected from the group consisting of alkali metal atoms and halogen atoms; with the provisos that when x is 1, y is 2 or 3; when y is 1, x is 2 or 3; when P is an alkali metal atom, Q is a halogen atom; and when Q is an alkali metal atom, P is a halogen atom.

29. The method of claim 28, wherein component (a') has formula

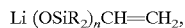

wherein n is 0 to 1,000; and component (b') has formula:

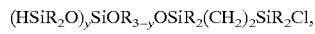

wherein y is 2 or 3.

30. A method of forming a hyperbranched polymer, wherein the method comprises polymerizing a macromonomer with a catalyst comprising a group VIII metal; wherein the macromonomer has general formula

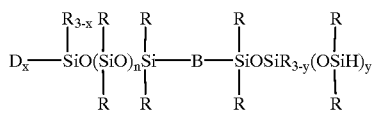

wherein D is an aliphatically unsaturated organic group, each R is independently selected from the group consisting of monovalent hydrocarbon groups with no aliphatic unsaturation and monovalent halogenated hydrocarbon groups with no aliphatic unsaturation; B is selected from the group consisting of an oxygen atom and a divalent hydrocarbon group of at least two carbon atoms and with no aliphatic unsaturation; n is an integer with a value greater than or equal to 0; x is 1, 2, or 3; y is 1, 2, or 3; with the provisos that when x is 1, y is 2 or 3 and when y is 1, x is 2 or 3.

31. The method of claim 30, wherein x=1 and y=2 or 3.

32. The method of claim 31, wherein the method further comprises adding a volatile Si—H containing compound to the hyperbranched polymer.

33. The method of claim 32, wherein the volatile Si—H containing compound is selected from the group consisting of trimethylsilane and tetramethyldisiloxane.

34. The method of claim 31, wherein the method further comprises extracting group VIII metal-containing compounds form the hyperbranched polymer using an immiscible nitrogen-containing polar solvent.

35. The method of claim 34, wherein the polar solvent is selected from the group consisting of tetramethylethylenediamine, polyethylenepolyamine, and acetonitrile.

36. A hyperbranched polymer prepared by the method of claim 32.

37. A hyperbranched polymer prepared by the method of claim 34.

* * * * *